United States Patent [19]

Mitchen et al.

[11] Patent Number: 5,070,886
[45] Date of Patent: Dec. 10, 1991

[54] BLOOD COLLECTION AND TESTING MEANS

[75] Inventors: Joel R. Mitchen, Mundelein; Sidney T. Smith, Lake Forest; Carl W. Jones, Hinsdale, all of Ill.

[73] Assignee: Safety Diagnostice, Inc., Evanston, Ill.

[21] Appl. No.: 540,664

[22] Filed: Jun. 19, 1990

Related U.S. Application Data

[63] Continuation-in-part of Ser. No. 147,138, Jan. 22, 1988, abandoned, and Ser. No. 411,083, Jan. 22, 1989, Pat. No. 5,014,718.

[51] Int. Cl.⁵ .................................................. A61B 5/00
[52] U.S. Cl. ..................................................... 128/771
[58] Field of Search ......................... 128/760, 763–765, 128/770, 771

[56] References Cited

U.S. PATENT DOCUMENTS

| | | | |
|---|---|---|---|
| 3,068,855 | 12/1952 | Furlong, Jr. ........................... | 128/2 |
| 3,672,368 | 6/1972 | Schwarz .......................... | 128/218 N |
| 3,828,775 | 8/1974 | Armel ............................. | 128/218 N |
| 4,151,832 | 5/1979 | Hamer ................................. | 128/765 |
| 4,436,098 | 3/1984 | Kaufman ............................. | 128/766 |
| 4,637,403 | 1/1987 | Garcia et al. ....................... | 128/770 |
| 4,643,200 | 2/1987 | Jennings, Jr. ....................... | 128/763 |
| 4,660,570 | 4/1987 | Dombrowski ...................... | 128/765 |
| 4,844,098 | 7/1989 | Mitchen ............................. | 128/765 |

FOREIGN PATENT DOCUMENTS

| | | | |
|---|---|---|---|
| 0164148 | 10/1985 | European Pat. Off. ............ | 128/770 |
| 8504089 | 9/1985 | World Int. Prop. O. .......... | 128/770 |

Primary Examiner—Max Hindenburg
Attorney, Agent, or Firm—Quarles & Brady

[57] ABSTRACT

A relatively painless method of safely collecting and testing blood which comprises piercing a patient's skin and collecting any blood and other fluids on a test disk moistened with a vehicle liquid. Several embodiments of a novel disposable apparatus having a reservoir of vehicle liquid for use in practicing the method also are described.

10 Claims, 2 Drawing Sheets

BLOOD COLLECTION AND TESTING MEANS

RELATED CASES

The present application is a continuation-in-part of copending application U.S. Ser. No. 07/147,138 filed Jan. 22, 1988 now abandoned and copending application U.S. Ser. No. 07/411,083 filed Jan. 22, 1989, now U.S. Pat. No. 5,014,718.

FIELD OF THE INVENTION

The present application relates to the collection and testing of cutaneous blood and blood components. More particularly, it relates to a method and apparatus for the safe, minimally-invasive, relatively painless, transcutaneous, concurrent collection of a blood sample and the testing of blood components.

DESCRIPTION OF THE PRIOR ART

To date, researchers and clinicians requiring a sample of the blood for testing of an animal or human have usually obtained that sample by either piercing or nicking the skin of the human or animal and then collecting the sample from a vein, capillary or artery. At times the sample is collected with the assistance of a vacuum. The sample is then processed and a diagnostic test run separately. The method is painful.

Existing devices have sought to make the acquisition of the sample more convenient. Typically these devices perform a fingerstick procedure using a spring loaded apparatus to thrust a lancet into a fingertip at high speed. A lancet is loaded in the device and the action is cocked, the finger to be pierced is held against a platform, and a button is pushed releasing the spring loaded action and piercing the finger automatically. Examples of these devices include the Monojector (U.S. Pat. No. 4,503,856), manufactured by Monoject Company, the Autolet (U.S. Pat. No. 4,230,118), manufactured by Owen Mumford Limited, and similar devices by Becton-Dickson, Bio-Dynamics, and others.

All of these devices pierce the skin automatically but rely upon the subject or a technician to force the blood from the puncture site by squeezing the fingertip. This milking action can be painful. Dombrowski (U.S. Pat. No. 4,653,513), seeks to reduce the pain and eliminate the need for milking the blood from the puncture site by the use of vacuum to collect a droplet of blood. The apparatus disclosed would also permit blood collection from a less vascularized area. However, the device makes a conventional puncture, which yields a substantial amount of blood (up to 0.5 milliliters), more than is required for many diagnostic tests. The excess blood, which may be contaminated with any of a number of infectious agents such as Hepatitis A, B, and C, or HTLV of Acquired Immune Deficiency, must then be disinfected thereby exposing the technicians performing this procedure to the risk of infection.

Conventional lancing devices (including Dombrowski) address acquisition of the blood sample. That sample must then be transported to the site where the diagnostic test will be performed. The sample may then be processed in a variety of ways before the diagnostic test is performed. Once the test is performed, the test system and the contaminated collection devices must be disposed of, frequently by inconvenient methods.

Hutcheson (European Patent Application, 0164148, 11 December 1985), disclosed a device where the diagnostic test system and lance are contained within a kit, whereby the subject is lanced and then immediately transfers a sufficient amount of blood to the test strip. The apparent advantage of such a system is the elimination of the transportation step. However, the procedure is stepwise and indistinguishable from the current practices.

Palmer (International Application WO 85/04089, 26 September 1985), disclosed a device and method for the simultaneous collection and processing of a blood sample. The apparatus disclosed in Palmer comprises a puncturing device within a chamber containing a liquid which is the reagent system employed by the test. Palmer addresses the simultaneous collection and processing of a blood sample. However, the device can only be used for tests with liquid reagents which are stable for long periods of time in liquid form. Because such liquid reagent systems are not typically stable at room temperature very long, this limits the practical application of such a system. The puncture employed by Palmer is a conventional puncture such as that employed by Monoject, Autolet, and others, which will leave a wound site which must be disinfected and covered until bleeding has ceased.

It would be advantageous to have a method and apparatus for the relatively painless collecting, and testing of blood, employing diagnostic reagents stable for long periods of time, with little risk of fluid contact by the nurse or the phlebotomist performing the service, and with less trauma to the patient.

SUMMARY OF THE PRESENT INVENTION

It is the general object of the present invention to disclose a safe, minimally-invasive, relatively painless method and apparatus for the collection, and testing of blood for specific components.

Briefly stated, the method of the present invention comprises pretreating the external surface of an area of the skin of a human or animal to anesthetize it and to make it antiseptic; piercing the skin in that area, without significant pain; collecting a sample comprising blood and body fluids from the area on a test medium moistened with a vehicle liquid; and testing the sample for one or more diagnostic purposes. The method requires only a very small (several microliters) amount of blood. No excess is collected, wasted or spread. In addition, the procedure is essentially painless. If desired, the method can include inactivating any virus that may be present in the sample.

When the apparatus of the present invention is employed, neither the blood nor contaminated parts are exposed to spread disease. Furthermore the patient is not traumatically exposed to the piercing member, because it is hidden from the patient's view.

The apparatus of the present invention basically comprises a member having a supporting base with an upright piercing pin; a resilient, collapsible cover attached at the bottom to the base and having an open top; a porous test disk, which may contain test reagents which will react with specific substances if they are present; and a reservoir which contains a vehicle liquid which is used to moisten the porous test disk and to transport the blood from the pierced area to the test disk. The apparatus also may include a protective cap and seals and means for dulling nerve endings by pressure dispersal.

In one embodiment of the apparatus the reservoir for the vehicle liquid is in a chamber formed by the base and the cover of the apparatus. In another embodiment, the reservoir is in an overcap which may be connected to main portion of the apparatus.

Objects and advantages, in addition to those described, will become apparent to those skilled in the art from the description and drawings.

DESCRIPTION OF THE PREFERRED EMBODIMENTS

In FIGS. 1 to 4 of the drawings, there is shown one embodiment of an apparatus which can be used in the practice of the method of the present invention.

Figure 1:
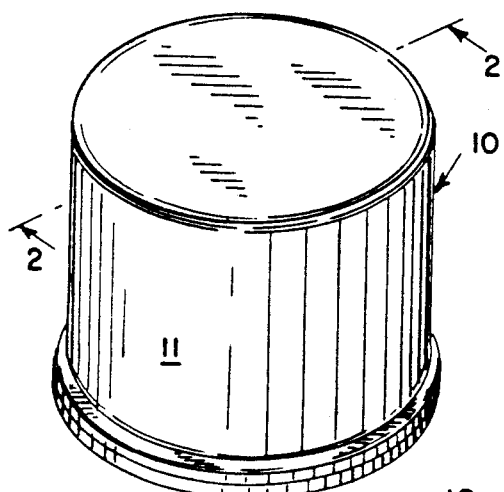
FIG. 1 is a perspective view of a first embodiment of the apparatus of the present invention packaged prior to use.
Figure 2:
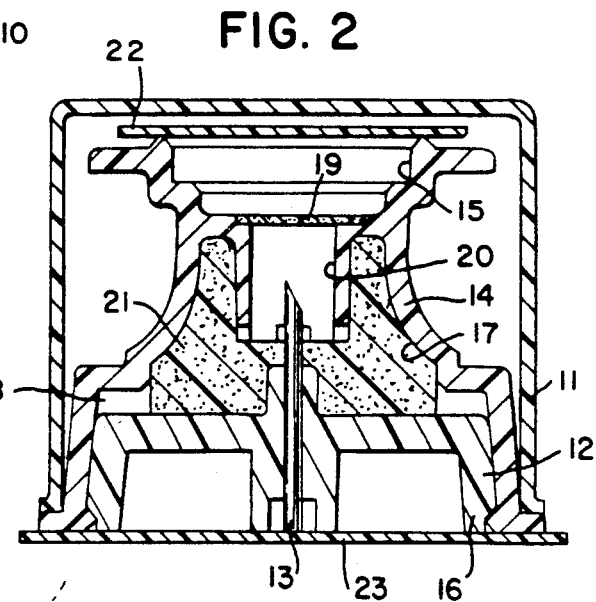
FIG. 2 is a sectional view taken along lines 2—2 of FIG. 1.

Referring to FIGS. 1 and 2, it can be seen that the apparatus 10 is protected prior to use by a cap 11. As seen in FIG. 2, the apparatus 10 includes a supporting base 12 with an upright piercing pin 13. The apparatus 10 also includes a resilient, collapsible cover 14 which has a cup-shaped top 15 and which is sealed at its bottom 16 to the base 12. The resilient, collapsible cover 14 and the base 12 form an internal reservoir 17 for a vehicle liquid 18.

Figure 3:
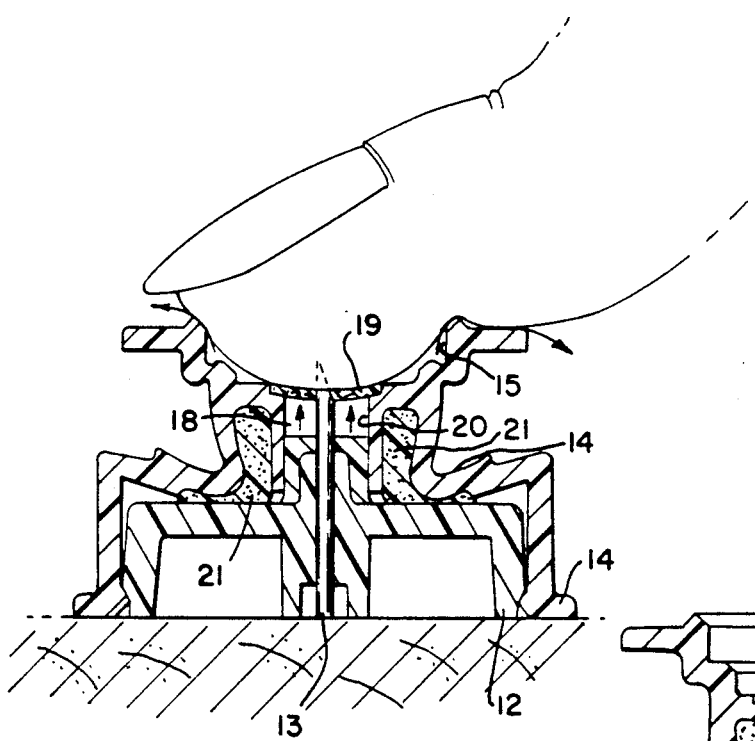
FIG. 3 is a schematic view showing the apparatus being collapsed and used in the practice of the method of the present invention.
Figure 4:
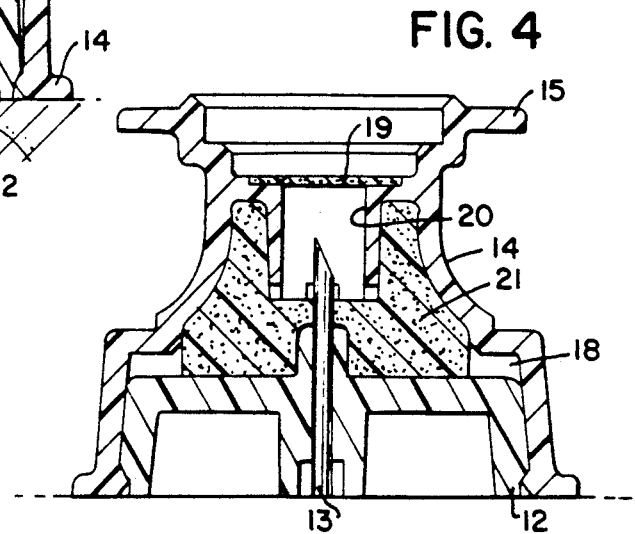
FIG. 4 is a view showing the apparatus after the skin has been pierced, and the apparatus is no longer collapsed.

As seen best in FIGS. 2, 3 and 4, the open top 15 of the cover 14 is closed by a porous test disk 19.

Referring to FIGS. 2 and 4, it can be seen that the piercing pin 13 is positioned directly below the open top 15 of the cover 14 and it extends into the open mouth of a tubular projection 20 which depends downwardly from the cover 14.

The apparatus 10 may be supplied sterile with a sponge 21 containing a vehicle liquid 18 in the reservoir 17. The apparatus is then protected from contamination by the outer cap 11, the top seal 22 and the bottom seal 23 which are best seen in FIG. 2.

Figure 5:
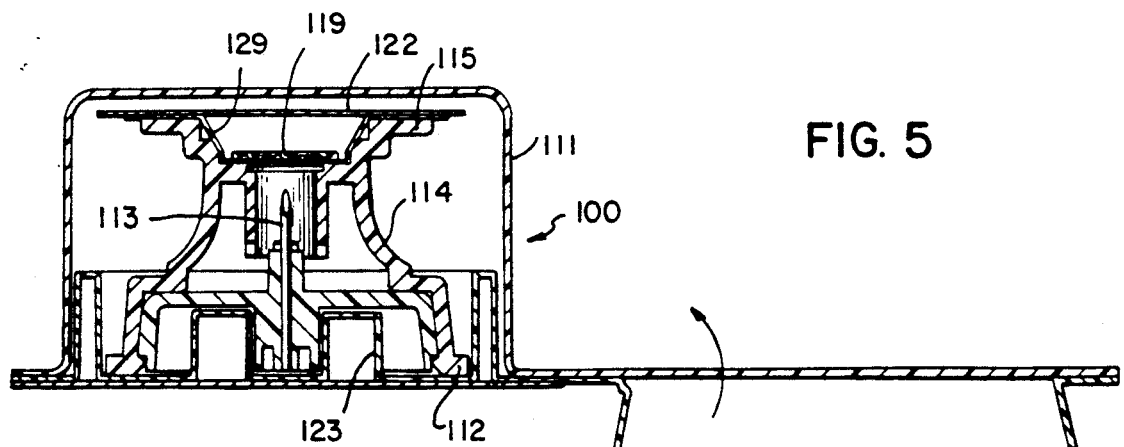
FIG. 5 is a perspective view, partly in section, of a second embodiment of the invention with the reservoir in an overcap.
Figure 6:
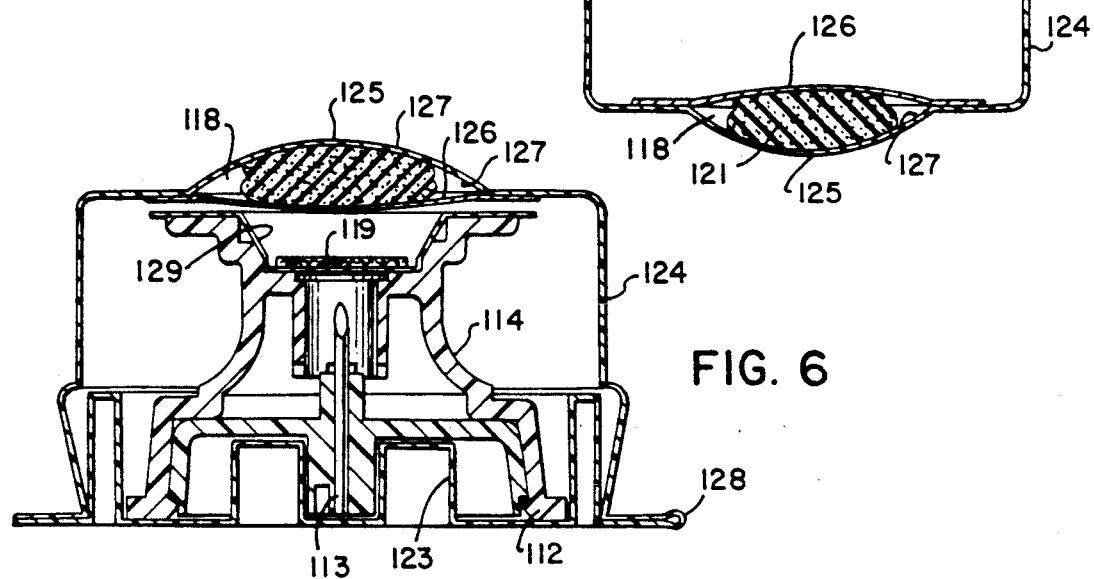
FIG. 6 is a schematic view of the embodiment of FIG. 5 with the overcap in place.
Figure 7:
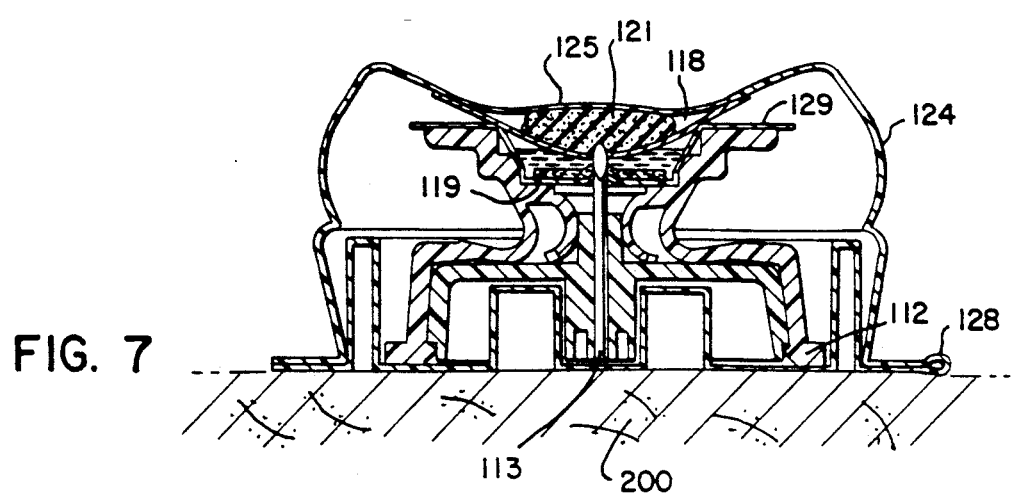
FIG. 7 shows the reservoir being pierced so that the disk can be wetted.

To use the apparatus 10, the cap 11 and top seal 22 are first removed. The apparatus 10 is then placed, as seen in FIG. 3, upon an unyielding surface 200 and the finger of the patient from whom the sample is to be collected is placed in the cup-shaped top 15 of the apparatus 10. The skin of the finger, which has been previously sterilized and anesthetized, is then pierced by pressing the finger down on the top of the apparatus 10 until the cover 14 collapses and the piercing pin 13 pierces the skin. The nerve endings in the area to be pierced are further dulled by the pressure dispersal; thus making the piercing relatively painless. The pierced skin area is bathed in vehicle liquid 18 which is forced from the sponge 21 in the reservoir 17 up the tubular projection 20 through the porous test disk 19. At the same time any air in the cup-shaped top 15 is forced out. The flow patterns of the vehicle liquid and the air are shown by arrows in FIG. 3. After the skin has been pierced, the finger is kept in contact with the cup-shaped top 15 and the downward pressing force is relieved allowing the cover 14 to resume the uncollapsed position seen in FIGS. 2 and 4. As the cover 14 assumes its original position a vacuum or area of reduced pressure is created in the reservoir 17 and a mixture of the vehicle liquid and any blood from the pierced area are drawn back onto and through the test disk 19. In the preferred embodiment of the invention, the disk 19 contains reagents which will react with specific substances, if present, in the blood to effect a color change. The results of the tests can be read visually or read by mechanical or electrical means. In FIGS. 5 and 6 a second embodiment of the apparatus is shown in which the "wet" components are separated in as much as practical from the "dry" component (i.e., the test disk) so that the risk of premature degradation of the test disk due to moisture vapor is avoided.

The apparatus 100 shown in FIGS. 5 and 6, like the embodiment of FIGS. 1-4, includes a cap 111, a supporting base 112, an upright piercing pin 113, a resilient collapsible cover 114 with a cup-shaped top 115, a porous test disk 119 and seal 122. In addition, the second embodiment includes an overcap 124 which has a domed top 125. The dome top 125 works with a moisture impervious seal 126 to form a chamber 127 which contains a sponge 121 with a vehicle liquid 118 comprising the "wet" compartment. The overcap 124 is preferably hingedly connected at 128 to the bottom housing 123. A barrier membrane 129 is present to form in concert with seal 122 a hermetic capsule contained within the chamber of the cup-shaped top 115. This hermetic capsule contains and preserves the dry component (i.e., the test disk) and may be filled with a dry inert gas (e.g., Nitrogen or Argon). The apparatus is stored in the condition seen in FIG. 5 until time of use. In less demanding applications, it may be preferable to store the package as shown in FIG. 6.

At the time of use the package (whether stored as shown in FIG. 5 or 6) is opened and the peelable seals 122 and 126 are removed. The overcap 124 is swung up and over the top 115 as seen in FIG. 6 and the domed top 125 is depressed, wetting the porous test disk 119 with vehicle liquid 118. Any excess vehicle liquid is removed by the blotting action of the sponge 121 as it returns to its uncompressed position. The overcap 124 can then be swung back out of the way and the apparatus will be ready to be used in the manner seen in FIG. 3. Alternatively, only the top seal 122 is removed and the overcap 124 swung up and over the top 115 as seen in FIG. 6. When thus assembled, the domed top 125 can be depressed so that the piercing pin 113 will pierce the seals 129 and 126 and the vehicle liquid 118 will flow into contact with and wet the porous test disk 119. When the disk 119 is sufficiently wetted, the overcap 124 can be swung back out of the way and the apparatus will be ready to be used in the manner seen in FIG. 3.

The moisture impervious seals of the apparatus may be made of foil or any similar material that is satisfactory to prevent moisture transmission under the conditions of use and may be peelable.

Although specific devices for piercing the skin and collecting and testing the blood components have been described, it will be apparent to those skilled in the art that the apparatus of the invention may take other forms.

In the preferred practice of the method of the present invention, the skin is first pretreated with a solution containing anesthetic and antiseptic agents, such as Lidocaine hydro-chloride and benzalkonium chloride, respectively.

The pretreatment solution might be applied by spraying or in a gel-like binder, or with a bandage-like applicator. The solution could contain specific antiviral agents, or general antibacterial-antiviral-antifungal such as non-oxynol-9 (Decon Laboratories, Inc.), formal in or Betapropiolactone, Binary ethylenediamine, and Psoralen photochemical inactivation (Hyclone Laboratories, Inc,; *Art to Science,* Vol. 5, No. 3:4–5). The choice of chemical viral inactivator depends on which test will be made on the sample.

The preferred vehicle liquid contains a surface active agent, such as a nonionic detergent, and an anticoagulant agent to fluidize the sample to avoid coagulation and hemolysis, such as sodium heparin and saline. It may also contain solvents such as polyvinyl acetate, acetone and DMSO (Dimethylsulfoxide) to change the chemical nature of the sample, and analgesic and a gel or cream of high viscosity to help the cup-shaped top 15 form a seal with the skin. The vehicle liquid can also contain other anticoagulants or chelating agents and buffering with carrier molecules to avoid nonspecific losses due to binding or deterioration and to promote preservation and inactivate virus. The vehicle liquid also could contain chemicals to inactivate other potential pathogens. Alternately it could enhance or grow pathogens for testing or nonpathogens as a means of detection.

A typical vehicle liquid contains the following ingredients:

| Ingredients | Generic Name Active Component | Preferred Concentration | Concentration Range, Active |
| --- | --- | --- | --- |
| Heparin | Sodium Heparin | 50 IU/cc | 5–100 IU/cc |
| Saline Buffered Solution | Phosphate Buffered Saline Solution (Sodium Chloride) NaCl | 0.5M Buffer (pH 7.2) 0.45M NaCl | pH 4–8 0.2–0.9M |

COMPONENTS OF THE VEHICLE LIQUID

In addition, EDTA (0.1%) or even vasodilating compounds may be used, such as phenylephrine hydrochloride. Vasodilators are preferred if more blood cells as compared to immunoglobulins are desired. Vasorestrictors can be used to prevent further bleeding at the nick.

In addition, Triton X-100 or other surface agents providing the same function and not having any detrimental effects on the test but which will inactivate any virus that may be present can also be used. Representative of such surface active agents are the following: Nonidet P-40 (Shell Oil), guanidinium chloride,—mercaptoethanol or other nonionic detergents such as those listed in Stromber, K., "Surface-Active Agents for Isolation of the Core Component of Avian Myeloblastosis Virus". Journal of Virology 1972, pp. 684–697.

The preferred anticoagulant solution contains sodium heparin. However, other anticoagulants which may be used include the following: ethylenediaminetetraacetic acid (EDTA) (0.02%), ammonium heparin, sodium citrate, streptokinase or streptodornase. Carrier molecules can be added to prevent nonspecific absorption of desired components or to heal the pierced area.

Other anesthetic and antiseptic agents than Lidocaine (2.5% w/w), benzalkonium chloride (0.13% w/w) may be used. Other agents such as methyl salicylate (15.0%) in methanol (70% v/v), ethanol, paraben, methylparaben, providone iodine, phenol (0.5%) antibiotics, dimethyl sulfoxide, acetone, polyvinyl-acetate, polyvinyl alcohol, mineral oil, propylene glycol, or polyethylene glycol can be used. In addition, an anti-bubble agent may be added such as Pourite (Trademark of Analytical Products, Inc., U.S. Pat. No. 4,089,748).

If desired, a pain-depressing agent such as benzocaine or triethanolamine salicylate or a heat stimulating agent like methylsalicylate also may be included along with volatile solvents such as ether. Still further the addition of milk enzyme solutions such as trypsin may be useful to inactivate degrading enzymes, depending on the blood component desired in the eluent.

The preferred method of piercing the skin, collecting blood components and testing comprises:

A. Applying an anesthetic and antiseptic pretreatment solution with a pad to a portion of the tip of a finger for a few seconds;

B. Removing the protective cap 11 and top seal 22 and placing the base 12 of the apparatus 10 upon a supporting surface 200 as seen in FIG. 3;

C. Pressing the tip of a finger lightly on the cup-shaped top 15 of the apparatus to form a seal between the finger and the top 15;

D. Then piercing the skin by pressing firmly upon the top of the apparatus with the finger until the resilient cover 14 collapses and the piercing pin 13 pierces the test disk 19 and the skin of finger. The porous test disk 19 moistened by the vehicle liquid comes into contact with the skin and the blood and fluids flowing from the pierced skin;

E. Removing the downward pressure on the finger while keeping the finger in contact with the top 15 until the cover 14 assumes its uncollapsed state whereupon any blood and fluids are transferred by suction and adsorption to the test disk 19;

F. Wiping the skin area with alcohol or a suitable antiseptic; and,

G. Reading the results of the test.

The practice of the present invention is further illustrated by the example which follows:

EXAMPLE I

SUBJECT—Male, Age 47. A small area (about 2 cm$^2$) of the skin on the patient's finger is treated with Lidocaine, benzalkonium chloride for 10 seconds. The finger is then pressed down lightly upon the cup-shaped top 15 of an apparatus 10 containing about 200 microliters of buffered heparin in the sponge 21 in the reservoir 17. The finger is then pressed down to cause the side walls of the cover 14 to collapse and telescope whereupon the pin 13 pierces the skin of the finger and the area of piercing is bathed with vehicle liquid from the sponge 21. The downward pressure exerted on the apparatus is then relieved without lifting the finger whereupon the resilient cover resumes its original state creating a vacuum which sucks the vehicle liquid 18 and any blood through and onto the test disk 19 which contains the test reagents. The test results are then read.

In the preferred embodiments, the test reagents are on the disk 19. Alternatively, the apparatus 10 can be prepared without the test reagents being already on the test disk 19 and the reagents can be added after the collection of the blood sample.

TEST I

GLUCOSE is detected at about 5 mg/dl by a colorimetric reaction using a specific glucose-oxidase/peroxidase and guaiac chromaphore method.

TEST II

CHOLESTEROL is determined at about 100 mg/dl by a colorimetric reaction using a specific cholesterol esterasecholesterol oxidase—peroxidase and guaiac chromaphore method. The cholesterol test disks are made by mixing in sequence a binder of methylcellulose in water and propanol (50/50); a buffer of citric acid/sodium citrate dissolved in water, pH 6.5-7.0 with sodium taurocholate; an enzyme mixture of cholesterol esterase, cholesterol oxidase and peroxidase; and a chromogen comprised of gum guaiac in propanol. The mixture is applied to filter paper disks and dried to a moisture content of less than 0.2% for storage stability.

It will be apparent to those skilled in the art that there are many reasons why it may be preferable to use the present invention rather than to pierce the skin with a lance or needle followed by separate processing and testing. The procedure of the present invention is minimally invasive and therefore there is less chance of secondary infection because the apparatus can be supplied presterilized and used in a sanitary manner. Another advantage is that the method is relatively painless. In addition, the vehicle liquid and blood or other fluids may be obtained by the donor or another person in a one-hand operation, without technical expertise. Furthermore, the site of extraction is less precise than that required for phelbotomies. Therefore, a sample can be obtained more easily from infants or others with small or damaged veins or in emergency situations. Finally, the visual detection of test changes can be replaced by electronic detectors, if desired. For example, a hand-held colorimeter can be adapted to visualize the test disc within apparatus and then print out the test results.

The method and apparatus of the present invention are of value in diagnostic tests which require dilute plasma/serum for doctors/office, home health care and consumer performed diagnostics. An inexpensive apparatus specifically designed for a given test can be supplied completely assembled, sterile and filled with vehicle liquid by a manufacturer with the test filter in place so that all that is required is to use the device and read the results. The devices can then be disposed of without requiring further treatment to inactivate potential virus contaminants.

In addition, it will be apparent to those skilled in the art that the apparatus of the present invention makes it easier to collect blood from persons who are squeamish. With the apparatus of the present invention the lance, which can also be a cannula, is not visible at any time to the person from whom the sample is being collected.

It will be apparent to those skilled in the art that a number of modifications and changes can be made without departing from the spirit and scope of the invention. Therefore, the invention is not to be limited except by the claims.

We claim:

1. An apparatus for use in a safe, minimally-invasive, painless method of safely collecting and testing blood and body fluids from a patient which comprises: a piercing pin mounted on a base; a collapsible, telescoping cover having a cup-shaped top sealed at its bottom to the base; a porous test disk with dry reagents secured in the cup-shaped top; and a reservoir containing a liquid for moistening the disk, so that when a pressing force is exerted on the top with a finger, the telescoping cover will collapse permitting the liquid to moisten the disk and the finger to be pierced so that blood or other fluids are transferred onto said test disk.

2. An apparatus of claim 1 in which the porous test disk is encapsulated in barrier materials forming a hermetic chamber.

3. An apparatus of claim 2 in which the hermetic chamber is filled with an inert or non-reactive gas.

4. An apparatus of claim 2 in which the vehicle liquid reservoir is located in a chamber formed by the base and the telescoping cover and is proximal to the test disk.

5. An apparatus of claim 4 in which the apparatus is protected by a cap which is attached to the base.

6. An apparatus of claim 2 in which the vehicle liquid reservoir is in an overcap which fits over the cup-shaped top.

7. An apparatus of claim 6 in which the overcap is attached to the main portion of the apparatus.

8. An apparatus of claim 1 in which the dry reagents on the test disk when moistened will react with specific materials that may be present in the blood or other body fluids to produce a color change.

9. An apparatus of claim 1 in which the disk contains reagents that will react with blood to produce a detectable change.

10. An apparatus for use in a safe, minimally-invasive, painless method of safely collecting and testing blood from a patient which comprises: a piercing pin mounting on a base; a collapsible, telescoping cover having a cup-shaped top sealed at its bottom to the base; a porous test disk containing dry reagents under the cup-shaped top; and a reservoir containing a liquid for moistening the dry reagents disk, said reservoir being in an overcap which during storage is spaced from the top to keep the liquid separated from the dry reagents until immediately prior to use and which at time of use is placed over the top and used to moisten the dry reagents disk so that when a pressing force is exerted on the top with a finger, the telescoping cover will collapse permitting the finger to be pierced and blood or other fluids to be transferred onto said test disk.

* * * * *